United States Patent [19]

Hill

[11] Patent Number: 5,403,258
[45] Date of Patent: Apr. 4, 1995

[54] ABDOMINAL AND LUMBAR THERAPY AND EXERCISE APPARATUS

[76] Inventor: Kent R. Hill, 1524 Alexander Cr., Pueblo, Colo. 81001

[21] Appl. No.: 191,092

[22] Filed: Feb. 3, 1994

[51] Int. Cl.⁶ .......................................... A63B 101/00
[52] U.S. Cl. .................................. 482/192; 482/140; 482/145
[58] Field of Search .................. 606/240, 242, 241; 601/56; 297/423.41, 461; 5/633, 648; 482/140, 142-144, 145, 148; D21/349, 191

[56] References Cited

U.S. PATENT DOCUMENTS

| | | |
|---|---|---|
| Re. 28,130 | 8/1974 | Hudson . |
| D. 280,922 | 10/1985 | Sieder .................. D21/191 |
| D. 320,824 | 10/1991 | Cordon .................. D21/191 |
| D. 339,617 | 9/1993 | Harashima ............ D21/191 |
| 2,240,228 | 4/1941 | Schall . |
| 2,425,971 | 8/1947 | Walker . |
| 3,010,719 | 11/1961 | Johnson . |
| 3,203,415 | 8/1965 | Moore .................... 601/56 |
| 3,682,475 | 8/1972 | Walker . |
| 3,787,049 | 1/1974 | Rellinger . |
| 4,241,915 | 12/1980 | Noble et al. . |
| 4,508,335 | 4/1985 | Kelley . |
| 4,611,806 | 9/1986 | Terry .................... D21/191 |
| 4,638,995 | 1/1987 | Wilson . |
| 4,974,832 | 12/1990 | Dalebout . |
| 5,009,417 | 4/1991 | Sarkozi . |
| 5,031,905 | 2/1991 | Walsh . |
| 5,120,052 | 6/1992 | Evans .................... 482/140 |
| 5,176,603 | 1/1993 | Hundley . |
| 5,190,513 | 3/1993 | Habing . |
| 5,217,487 | 6/1993 | Engel et al. ........... 606/240 |

*Primary Examiner*—Stephen R. Crow
*Assistant Examiner*—Jerome Donnolly
*Attorney, Agent, or Firm*—Frank P. Grassler

[57] ABSTRACT

A portable exercise and therapy device for the muscles of the lower back and the muscles of the abdomen. A framework in the shape of a parallelogram supports a cushion maintaining a constant angle of 131 degrees between the lower back of the user and the upper legs of the user. The cushion can contain a lower back massager and an elastic band adapted to hold hot or cold packs for application to the lower back. A variety of exercises can be performed on the device that tend to strengthen the muscles of the abdomen and the lower back.

8 Claims, 2 Drawing Sheets

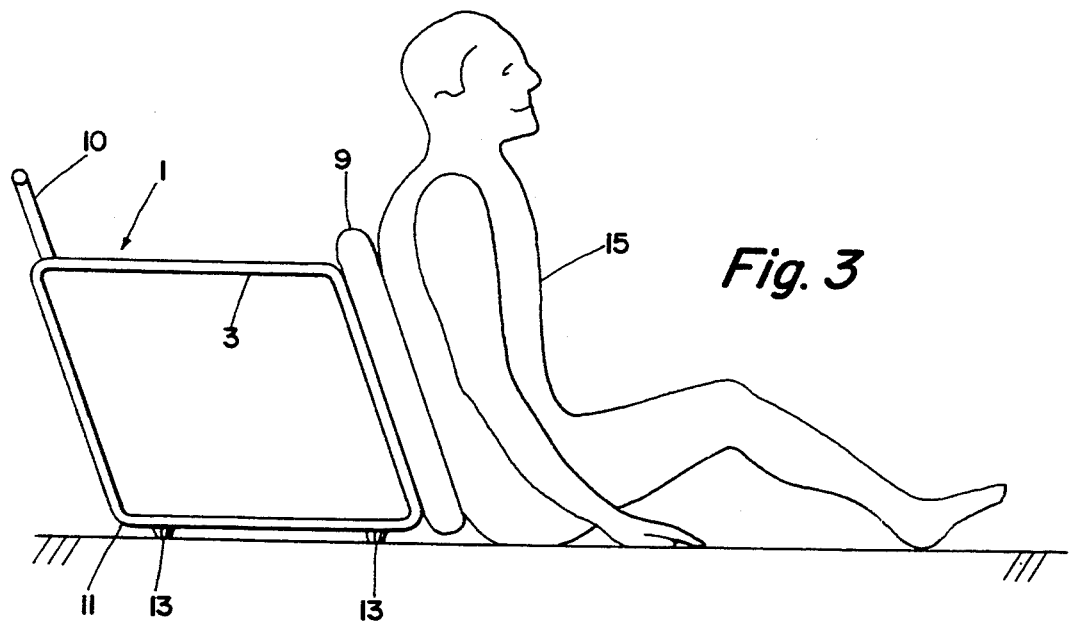
Fig. 3
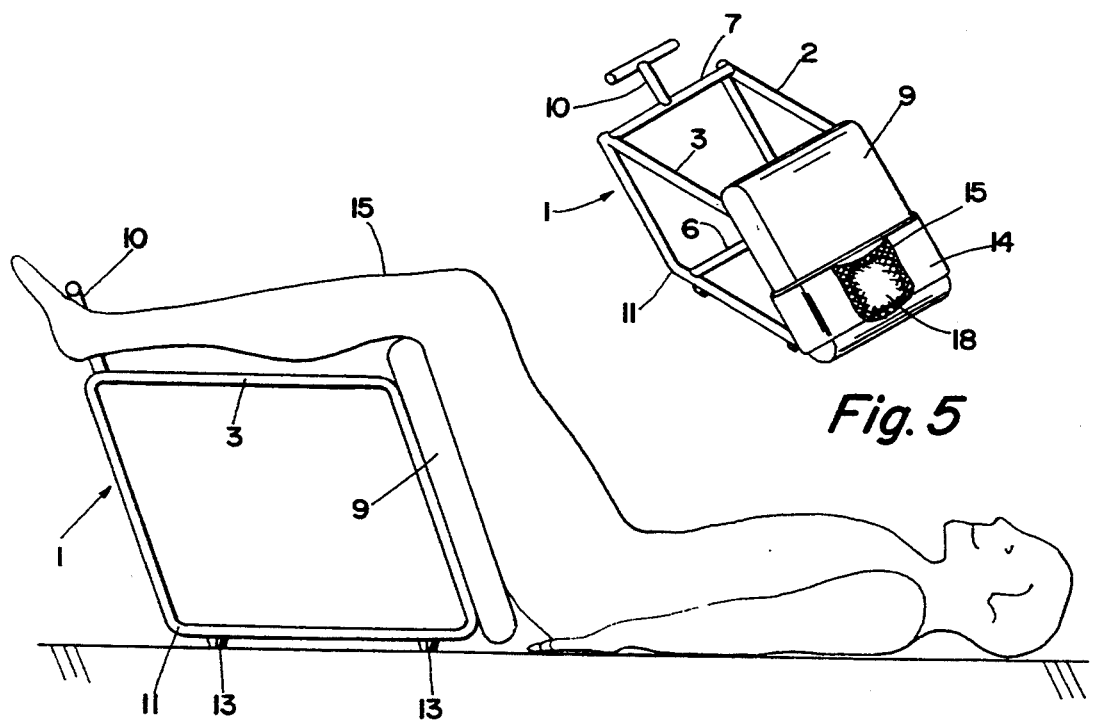
Fig. 5
Fig. 4

ABDOMINAL AND LUMBAR THERAPY AND EXERCISE APPARATUS

BACKGROUND OF THE INVENTION

This invention relates to devices of the class used for exercising the muscles of the lumbar region of the back and the muscles of the abdomen. The invention further is used to render therapy to the muscles of the lumbar region of the back.

The invention has for its primary object the goal of providing exercise for the various groups comprising the musculature of the human abdomen and the musculature of the lumbar region of the back. Another object of the invention is to provide a user with lower back exercise at an angle of the user's torso relative to the user's legs of approximately 131 degrees. Another object of the invention is to provide means by which a user can exercise the muscles of the abdomen without requiring assistance to hold the user's feet stationary. Ideally, the user should be able to perform exercises while placing both hands behind the head while securing the feet with some type of holding means and then performing a sit-up type of exercise. Another object of the invention is to provide for a multi-purpose exercise/therapeutic device.

Another object of the invention is to provide, in an alternative embodiment, a device for imparting various therapeutic modalities to the muscles of the lumbar region of the lower back.

SUMMARY OF THE INVENTION

The present invention, an exercise and therapy device, comprises first and second substantially planar support members; a plurality of connecting cross members, each connecting cross member being fixably attached at two points of attachment, said first point of attachment being at a point on said first substantially planar support member and said second point of attachment being at a point on said second substantially planar support member such that said planar support members and said connecting cross members form a framework having frontal and rearwards aspect; a substantially planer user support member or substantially planar testing member that contacts a portion of the anatomy of a user of the exercise device, said resting member being fixably attached at and substantially coplanar with said frontal aspect of said framework; and means for engaging the lower extremities of a user of the exercise device, said means fixably attached to a connecting cross member.

A more preferred embodiment of the exercise and therapy device comprises first and second substantially trapezoidal support members, said members having a planar aspect, said members being substantially parallel in said planar aspect, said members each having one of their four corners characterized in being substantially rounded off sufficiently to form a fulcrum about which rocking motion of the device can be obtained; a plurality of connecting cross members, each connecting cross member being fixably attached at two points of attachment, said first point of attachment being at a corner of said first parallel trapezoidal support member and said second point of attachment being at a corresponding corner of said second parallel trapezoidal support member, such that said trapezoidal support members and connecting cross members form a cuboidal framework having a frontal planar aspect and a rearwards planar aspect, there being upper and lower connnecting cross members for each of said frontal and rearwards planar aspects, said rounded off fulcrum corners being connected by the lower connecting cross member for said rearwards planar aspect; a substantially planar resting member that contacts a portion of the anatomy of a user of the exercise device, said resting member being fixably attached at and substantially coplanar with said frontal aspect of said framework; and means for engaging the lower extremities of a user of the exercise device, said means fixably attached to said upper connecting crossmember in said rearwards aspect.

BRIEF DESCRIPTION OF THE DRAWINGS

FIG. 3 is a side elevational view in partial section, not to scale, showing how a user can sit with their lower back against the invention, and can engage in a type of exercise wherein pushing against the exercise device will cause the device to tilt and rotate about the fulcrum 11 through arc 16. This view also demonstrates how massage therapy can be directed to the lower back of the user.

FIG. 4 is a side elevational view, not to scale, showing how a user can perform sitting-up exercises with the user's ankles engaged by T-bar or cross bar 10.

FIG. 5 is a frontal perspective view, showing the exercise/therapy device generally, in an embodiment having a belt across the user contact cushion that is adapted for the insertion of hot packs or cold packs for thermal therapy of the lower back.

DETAILED DESCRIPTION OF THE PREFERRED EMBODIMENTS

Figure 1:
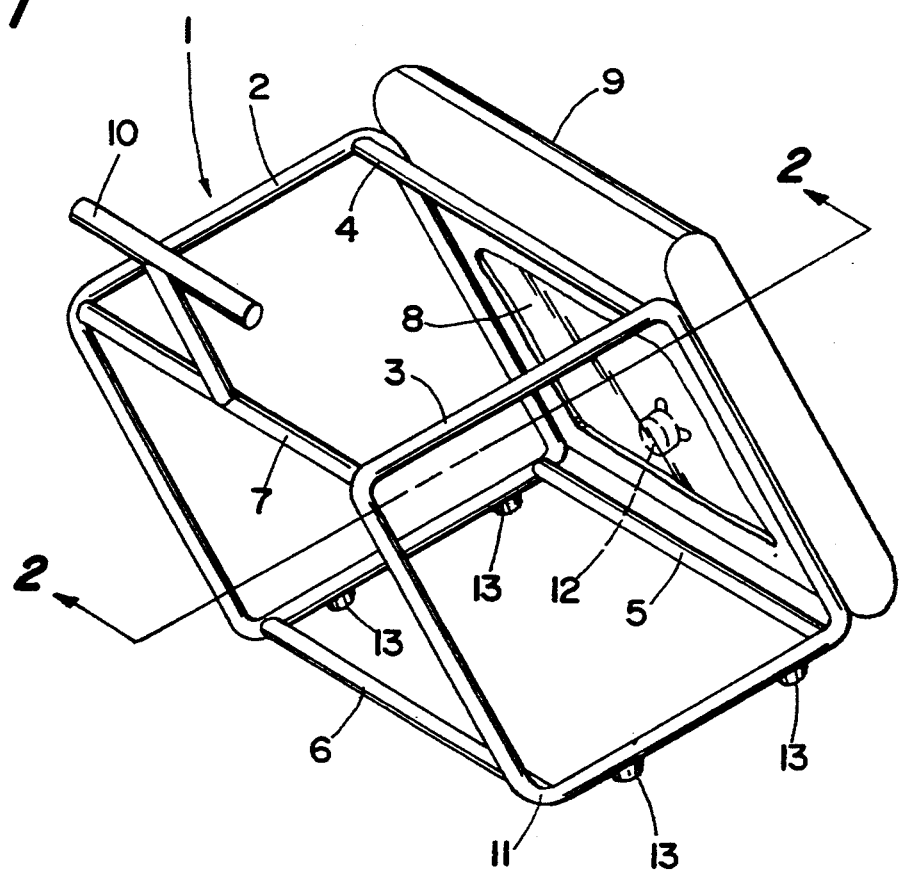
FIG. 1 is a perspective view, not to scale, showing the exercise/therapy device, in an embodiment having a massaging means mounted in the user contact cushion.
Figure 2:
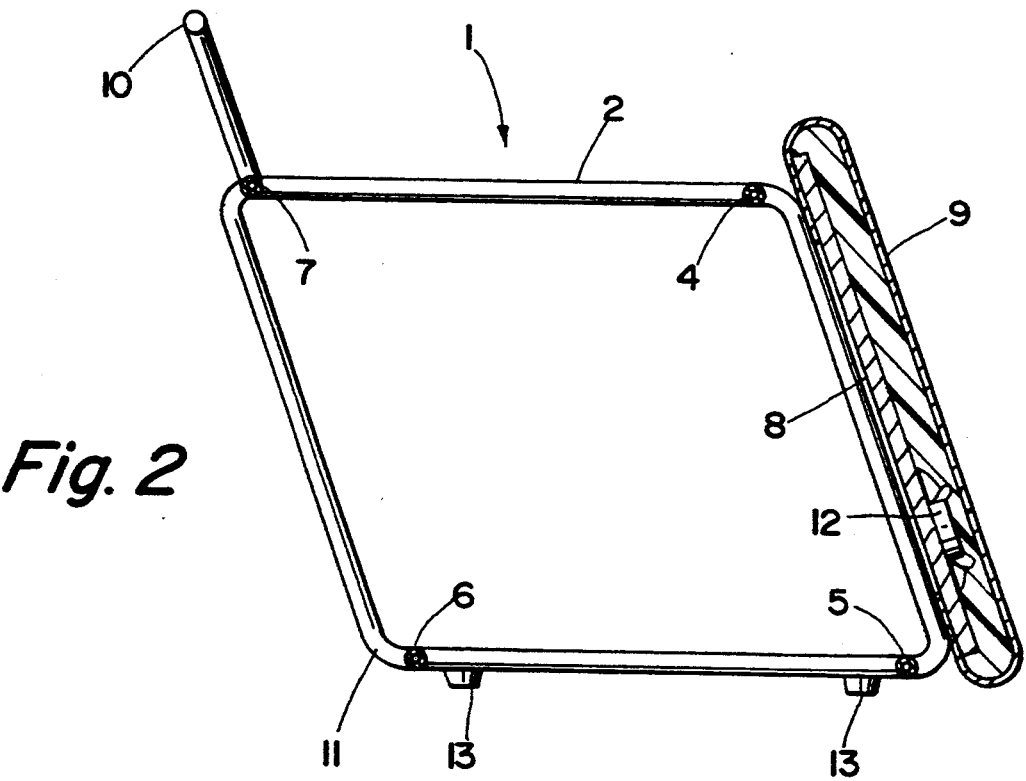
FIG. 2 is a side elevational view, not to scale, partially in section, showing the exercise/therapy device generally.

Referring firstly to Figures I and 2, there is shown generally the exercise and therapy device. A framework 1 is comprised of two groups of members. First and second trapezoidal support members 2 and 3 are formed of a suitably rigid material, preferably a metal and most preferably tubular steel or aluminum. Alternative materials would include suitably rigid thermoplastic or thermoset resins. The support members 2 and 3 are fixably held in substantially parallel planes with respect to each other by several cross member bars, 4, 5, 6 and 7. The cross member bars 4, 5, 6 and 7 are preferably fixably attached at corners formed by the support members 2 and 3. Hence, the support members 2 and 3 and the cross member bars 4, 5, 6 and 7 form the rigid framework 1.

The support members 2 and 3 generally will be trapezoidal or in the shape of a parallelogram. This is so since the support members 2 and 3 will have to support a backboard 8 and user cushion 9 that is oriented at an angle with respect to the floor when the invention is in use. Backboard 8 is fixably attached to the support members 2 and 3 and the upper and lower connecting cross members 4 and 5. The angle that the backboard 8 and user cushion 9 have with respect to the floor will be in a range of from 110 to 140 degrees, more preferably 125 to 135, and most preferably 131 degrees. The angle of 131 degrees is an anatomically ideal angle. This fact was discovered during studies on astronauts under conditions of zero gravity, or weightlessness. In such a weightless environment, when an astronaut would relax the muscles of the lower back, abdomen and upper legs, it was found that the angle between the torso and the upper legs generally was 131 degrees. Since this is the most natural angle that the human body finds to assume, it is also the angle most preferred for a user of the present invention to assume when seated against the cushion for either exercise or therapy.

The support members 2 and 3 are characterized further by each having one corner 11 that is rounded off so as to act as a fulcrum about which a rocking motion can be achieved. This rocking motion is described in conjunction with FIG. 4, which shows a seated user of the device. The user, with bent legs, would push upwards and backwards, thereby causing the device to rock about fulcrum 11 thus exercising key muscle groups in the upper legs, abdomen and lower back. The device is prevented from simply sliding backwards on the floor by a plurality of resilient feet 13 made of a suitable material that would impart sufficient friction to prevent such sliding. Suitable materials include soft or semi-soft thermoplastic resins.

Attached to upper rearward connecting member 7 is a means for engaging the lower extremities of the user of the device, such means most preferably being a T-bar 10 that is fixably attached to connecting member 7. In FIG. 5 it can be seen that a user of the device can lie on their back and perform sitting-up type of exercises with their ankles hooked under the T-bar 10 and the bottom of their upper legs resting up against the user cushion 9. Again, in the most preferred embodiment of the invention, the angle between the upper legs of the user and the user's lower back will be 131 degrees.

An important feature of the exercise and therapy device is the ability to perform physical therapy modalities on the musculature of the lower back. These modalities include massage, vibration, ultrasound, infrared, hot packs and cold packs. This is variously accomplished by having the appropriate device installed either fixably or removeably within or on the user cushion 9 or seated within pocket 15 of cross band 14. Massage machines, vibratory apparatus, ultrasound sources or infrared sources can be variously installed in the cushion 9. These different types of machines or apparatus are well known to those of ordinary skill in the art and a given type can be installed according to the therapeutic need to be addressed. Hot packs or cold packs 18 can be inserted into pocket 15 of cross band 14. Alternatively, a hot or cold pack 18 can be inserted directly underneath the cross band 14. The cross band 14 is preferably elastomeric fabric to accomodate bulky packs of irregular shape and size, and the cross band is fixably attached to cushion 9 according to means well known to the upholsterer's art.

An additional useful feature of the invention is a handle means by which a second person can grasp the exercise and therapy device and hold it so as to be able to position the massage means 12 over an area of a patient's back that would benefit from the massaging action. Thus, an assistant could grasp the invention by the handles, and hold the device over, for example, the thoracic area and slowly move the device over the patient's entire afflicted area to impart massage therapy to the area. The handles could advantageously be affixed onto first and second trapezoidal support members 2 and 3.

While the invention has been described and illustrated with reference to certain preparative embodiments thereof, those skilled in the art will appreciate that various changes, modifications and substitutions can be made therein without departing from the spirit and scope of the invention. It is intended, therefore, that the invention be limited only by the scope of the claims which follow, and that such claims be interpreted as broadly as is reasonable.

What is claimed is:

1. An exercise and therapy device comprising:
a substantially planar user support
first and second substantially planar parallelogram support frame members of equal size, said support members each having a radius of curvature on at least one of the four corners of said support members forming a fulcrum about which a rocking motion of the device may be obtained,
a plurality of connecting cross members, each connecting cross member being attached along it's length at two points, to said support members, said first point of attachment being at each corner of said first support member and said second point of attachment being at a corresponding corner of said second support member such that said parallelogram support frame members and said connecting cross members form a cubical frame work having a frontal aspect, a rearward aspect, a lower support surface engaging aspect and an upwardly facing aspect, said user support means attached to and connected between the frontal aspects of said first and second support members in a substantially coplanar substantially vertical orientation so as to allow engagement of said device by a user,
a cross bar means fixedly attached to said cubical frame members at substantially the upward and rearward corner of said cubical frame member, a sufficient distance above said cubical frame so as to allow the users of the device to lie on their back and perform sit-up type exercise with their feet and ankles hooked under said cross bar means while the bottom of a user's upper legs rest against said vertically positioned user support and the back of said user rests upon the same supporting surface as supports said device and;
a means engaging said lower support surface engaging aspect of said cubical support frame so as to resist a sliding motion of said exercise device when placed on a support surface.

2. The device as claimed in claim 1, additionally comprising a cushion that is fixably attached to said planar user support.

3. The device as claimed in claim 3, wherein the angle that is formed between a floor and the planar user support of the device when the device is placed on a floor, is in the range of 110 to 140 degrees.

4. The device as claimed in claim 1, wherein said cross bar means is a T-bar fixably attached to the upper rearwards connecting cross member.

5. The device as claimed in claim 3, wherein the angle that is formed between a floor and the planar user support of the device when the device is placed on a floor, is in the range of 125 to 135 degrees.

6. The device as claimed in claim 5, wherein the angle that is formed between a floor and the resting member of the device when the device is placed on a floor, is 131 degrees.

7. The device as claimed in claim 2, additionally comprising a holding strap that crosses over said cushion and is sufficient to removably hold a cooling or heating means for imparting thermal therapy to the lower back region of a user of the device.

8. The device as claimed in claim 2, additionally comprising means for achieving massaging motion in the area of the lower back of a user of the device, said massaging means being fixably mounted in the cushion of the device.

* * * * *